United States Patent [19]

Stevenson

[11] Patent Number: 4,526,899

[45] Date of Patent: Jul. 2, 1985

[54] EYE OINTMENT FORMULATION INCLUDING THE DISODIUM SALT OF 1,3-BIS(2-CARBOXYCHROMON-5-YLOXY)-PROPAN-2-OL

[75] Inventor: Neil A. Stevenson, Nanpantan, England

[73] Assignee: Fisons plc, Ipswich, England

[21] Appl. No.: 505,984

[22] Filed: Jun. 20, 1983

[30] Foreign Application Priority Data

Jul. 2, 1982 [GB] United Kingdom ............... 82/19185

[51] Int. Cl.$^3$ .............................................. A61K 31/35
[52] U.S. Cl. .................... 514/456; 514/912; 514/969
[58] Field of Search ........................................ 424/283

[56] References Cited

U.S. PATENT DOCUMENTS 2,725,334 11/1955 Conrad ................................... 424/70
4,401,663 8/1983 Buckwalter et al. ............... 424/321
4,424,205 1/1984 La Hann et al. ...................... 424/72

FOREIGN PATENT DOCUMENTS 2634908 4/1977 Fed. Rep. of Germany .
1341094 12/1973 United Kingdom .

OTHER PUBLICATIONS

Chem. Abst. 54, 5007i (1960)–Tice et al.
Chem. Abst. 67, 84765x (1967)–Lekhter et al.
Chem. Abst. 79, 23588(t)(1973)–Hovanessian.
Chem. Abst. 94, 71185(r)(1981)–Elder.

Primary Examiner—Douglas W. Robinson
Attorney, Agent, or Firm—Marshall, O'Toole, Gerstein, Murray & Bicknell

[57] ABSTRACT

There is described a sterile ointment basis, suitable for use in the eye, comprising one or more paraffins and acetylated lanolin.

There is also described an ointment comprising an active ingredient, e.g. an antiallergic drug, and the ointment basis.

There is further described a process for the manufacture in a medicament container of the ointment comprising an active ingredient.

6 Claims, No Drawings

EYE OINTMENT FORMULATION INCLUDING THE DISODIUM SALT OF 1,3-BIS(2-CARBOXYCHROMON-5-YLOXY)PROPAN-2-OL

This invention relates to novel pharmaceutical formulations and to a method for their production.

A large number of vehicles have been proposed for introducing medicaments into the eye. By far the most popular has been the aqueous solution. Thus 1,3-bis(2-carboxychromon-5-yl)propan-2-ol, and pharmaceutically acceptable salts thereof, have been proposed for use in the treatment of disorders of the eye by administration of aqueous pharmaceutical formulations (for example, British Pat. No. 1,399,834 and Australian Pat. No. 522,751). However, these formulations suffer from the disadvantage that they require frequent application, e.g. every 2 to 4 hours, and so are not suitable for overnight protection.

A wide variety of formulations and devices, e.g. lamellae, have been suggested to retain pharmaceuticals in the eye.

Viscous aqueous gel formulations, for example those based on polyethyleneglycol, hydroxypropylmethyl cellulose or polyvinyl alcohol, have a tendency to dry up, and form crusts around the eye. In addition, the rheological properties of the gel formulations can make application to the eye difficult. Furthermore, such aqueous formulations are frequently difficult to sterilise, lack stability, and require preservatives to prevent bacterial and fungal growth. Another eye ointment formulation that we have investigated, based on high molecular weight polythene dissolved in liquid paraffin, suffers from the disadvantage that on application to the eye it causes considerable blurring of vision, lasting up to half an hour, and is consequently unacceptable to the patient.

West German OLS No. 2,634,908, which relates principally to skin ointments containing pharmaceutically acceptable salts of 1,3-bis(2-carboxychromon-5-yloxy)-propan-2-ol also describes a paraffin based eye ointment. This paraffin based eye ointment suffers from the disadvantage that it lacks emolliency. An absorption ointment, containing the disodium salt of 1,3-bis(2-carboxychromon-5-yloxy)propan-2-ol in a base similar to Eye Ointment Basis BP is also disclosed in West German OLS No. 2,634,908.

Eye Ointment Basis BP suffers from the disadvantage that it contains lanolin, which is known to provoke allergic reactions in sensitive subjects, e.g. R. Breit and H-J Bandman, British Journal of Dermatology (1973) 88 414. A very large number of lanolin derivatives have been proposed as alternatives to lanolin for skin formulations, for example British Pat. No. 1,341,094 and U.S. Pat. No. 2,725,334. Derivatives of lanolin include dewaxed or liquid lanolins, acylated lanolins, ethoxylated lanolins, hydrogenated lanolins, transesterified lanolins, lanolin esters, and also derivatives of the saponification products of lanolin, that is lanolin acids and lanolin alcohols, for example acetylated lanolin alcohols. Martindale's Extra Pharmacopoeia, 28th Edition, p 1072, The Pharmaceutical Press, London, lists about 50 proprietary preparations of lanolin and lanolin derivatives.

Some of these derivatives, for example acetylated lanolin, whose synthesis is described in U.S. Pat. No. 2,725,334, have significantly different properties to lanolin. Thus acetylated lanolin and lanolin differ in that lanolin is hydrophilic and can absorb at least twice its own weight of water, whereas acetylated lanolin is hydrophobic, and has no tendency to absorb water. In addition, L. I. Conrad et al, J. Soc. Cosmetic Chemists, (1955) 6 344, Chem Abs. (1956) 50 (10) 7404 g state that lanolin facilitates the formation of water in oil emulsions, whereas the hydrophobic acetylated lanolin has little, if any, emulsifying ability. Several skin preparations in which lanolin has been replaced by lanolin derivatives have been described, e.g. M. G. Balsam et al, Cosmetics—Science and Technology, Vol. 1, 2nd Edition, page 146, Whiley-Interscience, New York disclose baby oils containing acetylated lanolin and acetylated lanolin alcohols, and F. Tice et al, J. Am. Pharm. Assoc., Pract. Pharm. Ed. (1959) 20 665, Chem Abs. (1960) 54 (5) 5007i describe a skin cream containing both lanolin and acetylated lanolin. However, there appear to be no disclosures relating to the use of acetylated lanolin in eye ointments.

Although the substitution of lanolin by lanolin derivatives may be successful for certain skin formulations including some ointments, there is no reason to suppose that similar substitutions in an eye ointment should result in an acceptable formulation, since the criteria of acceptability of skin formulations and eye formulation are quite different. In particular, the conjunctiva of the eye is bathed in a tear film, whereas the skin is essentially a dry surface.

We have now found an acceptable eye ointment which incorporates the hydrophobic lanolin derivative, acetylated lanolin.

Thus, according to the invention, we provide a sterile ointment basis, suitable for use in the eye, comprising one or more paraffins and acetylated lanolin.

The ointment basis may contain, as an active ingredient, a medicament. The active ingredient is preferably an anti-allergy drug, particularly 1,3-bis (2-carboxychromon-5-yloxy)propan-2-ol or a pharmaceutically acceptable salt thereof.

The pharmaceutically acceptable salt of 1,3-bis (2-carboxychromone-5-yloxy)propan-2-ol is preferably an alkali metal salt, especially the disodium salt.

Lanolin, also known as anhydrous lanolin, wool fat, wool wax and adeps lanae, is the purified anhydrous waxy substance obtained from the wool of the sheep, Ovis aries (Bovidae). It consists mainly of fatty acid esters of cholesterol, lanosterol and fatty alcohols. By acetylated lanolin we mean lanolin derivatives in which some, but not necessarily all, of the available hydroxy ester groups have been converted into acetoxy esters. We prefer acetylated lanolin in which from 40 to 100% of the available hydroxy groups of lanolin have been acetylated. We particularly prefer acetylated lanolin which has a hydroxyl value from 0 to 12, especially from 0 to 10.

The paraffins in the base may be selected from one or more of hard paraffin, soft paraffin and liquid paraffin. We prefer the base to contain soft paraffin, e.g. yellow soft paraffin BP, and liquid paraffin, e.g. liquid paraffin BP.

The composition may if desired contain an effective proportion of a pharmaceutically acceptable preservative or sterilising agent suitable for an ointment. Examples of preservatives which may be used are (i) Chlorbutol (2,2,2-trichloro-1,1-dimethyl ethanol hemihydrate), which may be present in the composition at 0.1 to 1.0%, e.g. about 0.5% w/w, (ii) methyl-p-hydroxybenzoate, either alone or in combination with propyl-p- hydroxybenzoate. The total concentration of hydroxybenzoate esters in the composition may range from 0.08% to 0.2% w/w.

We prefer the ointment basis to comprise a major proportion of a yellow soft paraffin, preferably from 70 to 90%, more preferably 75–85% and particularly 78 to 82% w/w.

We prefer the ointment basis to comprise a minor proportion of a liquid paraffin, preferably from 5 to 15%, more preferably 6 to 14% and particularly 8 to 12% w/w.

We prefer the ointment basis to comprise a minor proportion of acetylated lanolin, preferably 0.1 to 15%, more preferably 0.5 to 14% w/w and particularly 5 to 12% w/w.

The composition may contain from 0.1 to 30%, preferably 0.5 to 15% and more preferably 2 to 6% w/w of active ingredient.

The active ingredient is preferably used in micronised form, e.g. having a mean particle size below 30 microns, preferably in the range 0.01 to 10 microns.

Conventionally ointments and creams are manufactured by dispersing the active ingredients in the molten ointment basis, homogenising, cooling, and filling into suitable containers at room temperature. However, we have found that this method, for the ointments according to the invention, is problematic, and tends to produce unstable formulations which weep.

Surprisingly we have now found that by filling into medicament containers at a temperature greater than 50° C., satisfactory products are produced.

Thus according to the invention we further provide a process for the manufacture in a medicament container of an ointment according to the invention containing an active ingredient as hereinbefore defined, which comprises dispersing the active ingredient in the molten ointment basis according to the invention, and filling the resulting blend into the medicament container at a temperature greater than 50° C.

The active ingredient may be dispersed in the molten base using a stirrer, or preferably a blending apparatus. The molten base is preferably heated to about 80°–120° C., more preferably 100°–120° C., before dispersing the active ingredient. We prefer to sterilise the molten base before dispersing the active ingredient, e.g. by filtration through a suitable filter, such as a 1.2 micron filter.

The active ingredient may be dispersed in all of the base, or may be dispersed in a small amount of the base, followed by dilution of the dispersion with the remainder of the required base.

We prefer to sterilise the ointment, e.g. by heating to 150° C. for one hour, before filling into a medicament container.

We prefer the medicament containers to be sterilized before filling, e.g. by gamma irradiation or by exposure to ethylene oxide. The containers may be conventional containers for ointments, e.g. unit dose eye capsules, or preferably tubes. We particularly prefer tubes made of plastics materials, e.g. polyvinyl chloride, or a suitable maleable metal, e.g. aluminium. We prefer each of the tubes to be provided with a nozzle, suitable for applying an effective amount of the ointment to the eye.

The temperature for filling the medicament container is preferably from 50° to 70° C., more preferably from 55° to 65° C. and particularly from 58° to 62° C.

All operations are preferably performed aseptically in a sterile area.

According to our invention we also provide a method of treatment of conditions of the mammalian, e.g. human, eye in which conditions allergic or immune reactions play at least a contributory part, which method comprises administration of an effective amount of an ointment of the present invention to the eye of the mammal having such a condition.

The dosage to be administered will of course vary with the condition to be treated, with its severity and with the patient concerned.

The ointments according to the prevent invention are advantageous in that they are less allergenic, more stable, weep less, have improved rheological properties, more acceptable to the patient or longer acting than known ointments of similar formulation.

Conditions of the outer eye in which the method of the invention is indicated include vernal catarrh (vernal kerato-conjunctivitis) and marginal corneal ulceration or infiltration. Other conditions which may be treated by the method of the invention include the occular effects of hay fever, 'allergic eyes' where the allergen is known or unknown and spring/summer conjunctivitis. This latter term is used to mean allergic disorders of the eyes occurring in the spring and summer where an external allergen plays a part in the disorder. Further conditions of the eye which may be mentioned are 'irritable eye' or 'non-specific conjunctivitis', Herpes Simplex Keratitis and Conjunctivitis, Herpes Zoster Keratitis and Conjunctivitis, adenovirus infections, phlyctenular conjunctivitis, corneal homograft rejection, Trachoma, antirioruveitis and drug sensitivity.

The ointments according to the present invention are particularly advantageous in that they permit overnight treatment of these conditions.

The invention is further described, though only by way of illustration, in the following Example.

EXAMPLE

| | |
|---|---|
| Disodium salt of 1,3-bis(2-carboxychromon-5-yloxy)propan-2-ol (micronised) | 4.0% w/w |
| Yellow soft paraffin BP | 76.8% w/w |
| Liquid paraffin BP | 9.6% w/w |
| Acetylated lanolin ('Modulan' R) | 9.6% w/w |

METHOD

The disodium salt of 1,3-bis(2-carboxychromon-5-yloxy) propan-2-ol is added slowly in small portions, with vigorous mixing to a small portion of the preheated and sterilised components of the ointment basis at 90° C. When the addition is complete, mixing is continued for a further 15 minutes, and then the concentrated dispersion is sterilised by heating at 150° C. for 1 hour. The concentrated dispersion is then added to a homogeniser heated at 80°–100° C. and the remaining components of the ointment basis added slowly with continuous blending. When this addition is complete, the molten ointment is blended for a further 15 minutes and then cooled to a temperature of 58°–62° C. The ointment is then filled in pre-sterilised eye ointment tubes, which are crimped and allowed to cool to room temperature.

As used herein and in the appended claims, the abbreviation "BP" refers to the British Pharmacopoeia and indicates that a product so identified is defined therein. Soft paraffin refers to a purified mixture of semi-solid hydorcarbons obtained from petroleum. It is a white or pale yellow to yellow, translucent, soft, unctuous, slightly fluorescent mass, odorless when rubbed on the skin and almost tasteless. M.P. 38° to 256° C. Liquid paraffin is a purified mixture of liquid hydrocarbons obtained from petroleum, with an oily, unctuous feel; it is colorless and transparent, odorless and almost tasteless.

I claim:

1. An ointment for topical administration to the eye of a mammal for treatment of allergic conditions comprising:

0.5 to 15%, by weight of the total composition, of the disodium salt of 1,3-bis(2-carboxychromon-5-yloxy)propan-2-ol, as active ingredient, 70 to 90% by weight of soft paraffin, 5 to 15% by weight of liquid paraffin, and 0.1 to 15% by weight of acetylated lanolin in which 40 to 100% of the available hydroxy groups have been acetylated.

2. An ointment according to claim 1, wherein the acetylated lanolin has a hydroxyl value of 0 to 12.

3. An ointment according to claim 1, wherein the soft paraffin is yellow soft paraffin BP.

4. An ointment according to claim 1, wherein the liquid paraffin is liquid paraffin BP.

5. An ointment according to claim 1, containing 2 to 6% of the active ingredient.

6. An ointment according to claim 1, wherein the active ingredient has a mass particle size of 0.01 to 10 microns.

* * * * *